(12) United States Patent
Hendriks et al.

(10) Patent No.: US 11,129,691 B2
(45) Date of Patent: Sep. 28, 2021

(54) PULSED-LIGHT EMITTING MARKER DEVICE

(71) Applicant: KONINKLIJKE PHILIPS N.V., Eindhoven (NL)

(72) Inventors: Bernardus Hendrikus Wilhelmus Hendriks, Eindhoven (NL); Michael Grass, Buchholz In der Nordheide (DE); Thomas Koehler, Norderstedt (DE); Harold Agnes Wilhelmus Schmeitz, Eindhoven (NL); Roland Proksa, Neu Wulmstorf (DE); Vishnu Vardhan Pully, Eindhoven (NL); Marco Andreas Jacobus Van As, Waalre (NL); Waltherus Cornelis Jozef Bierhoff, Veldhoven (NL); Franciscus Marinus Antonius Maria Van Gaal, Heeze (NL); Drazenko Babic, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 452 days.

(21) Appl. No.: 15/535,455

(22) PCT Filed: Dec. 14, 2015

(86) PCT No.: PCT/EP2015/079513
§ 371 (c)(1),
(2) Date: Jun. 13, 2017

(87) PCT Pub. No.: WO2016/096675
PCT Pub. Date: Jun. 23, 2016

(65) Prior Publication Data
US 2017/0340406 A1   Nov. 30, 2017

(30) Foreign Application Priority Data
Dec. 16, 2014  (EP) .................................. 14198296

(51) Int. Cl.
*A61B 90/00* (2016.01)
*A61B 34/20* (2016.01)

(52) U.S. Cl.
CPC .............. *A61B 90/39* (2016.02); *A61B 34/20* (2016.02); *A61B 2034/2057* (2016.02); *A61B 2090/3945* (2016.02)

(58) Field of Classification Search
CPC ............ A61B 34/20; A61B 2034/2057; A61B 2090/3945; A61B 1/041; A61B 5/0059; A61B 2090/3937; A61B 2034/2055
See application file for complete search history.

(56) References Cited

U.S. PATENT DOCUMENTS 5,622,170 A * 4/1997 Schulz ................ A61B 5/0064
356/141.1
6,324,418 B1  11/2001 Crowley
(Continued)

FOREIGN PATENT DOCUMENTS

EP  2769667 A1  8/2014
JP  2003254716 A  9/2003
(Continued)

OTHER PUBLICATIONS

Rohm Semiconductor Data Sheet—SML-P11 Series, 2012.
(Continued)

*Primary Examiner* — Serkan Akar
*Assistant Examiner* — Aminah Asghar

(57) ABSTRACT

An active marker device (100) is introducible into a human tissue and for tracking a region of interest of a human body. The active marker device includes a light source (101) for emitting light such that the emitted light can be detected by an optical sensor. In this way, the active marker device and/or the region of interest can be tracked by a tracking system including the optical sensor. The active marker (Continued)

device (100) also includes a switch (102) for turning the light source on and off and for operating the light source in a pulsed mode.

23 Claims, 5 Drawing Sheets

(56) References Cited

U.S. PATENT DOCUMENTS

| | | | |
|---|---|---|---|
| 6,336,904 B1 | 1/2002 | Nikolchev | |
| 6,675,040 B1* | 1/2004 | Cosman | G06T 3/00 |
| | | | 600/427 |
| 7,899,544 B2 | 3/2011 | Cantlon | |
| 9,820,668 B2 | 11/2017 | Hua | |
| 2003/0012342 A1 | 1/2003 | Suhm | |
| 2004/0109823 A1* | 6/2004 | Kaplan | A61B 5/064 |
| | | | 424/1.11 |
| 2005/0049488 A1* | 3/2005 | Homan | A61B 1/00036 |
| | | | 600/431 |
| 2006/0036164 A1* | 2/2006 | Wilson | A61B 5/06 |
| | | | 600/424 |
| 2006/0142745 A1* | 6/2006 | Boutoussov | A61B 18/20 |
| | | | 606/10 |
| 2006/0173245 A1* | 8/2006 | Todd | A61B 1/0653 |
| | | | 600/178 |
| 2008/0171934 A1 | 7/2008 | Greenan et al. | |
| 2008/0246920 A1* | 10/2008 | Buczek | A61B 90/36 |
| | | | 351/221 |
| 2008/0255425 A1 | 10/2008 | Voegele | |
| 2011/0046438 A1* | 2/2011 | Iwaisako | A61B 1/00029 |
| | | | 600/101 |
| 2011/0166442 A1* | 7/2011 | Sarvazyan | A61B 5/06 |
| | | | 600/424 |
| 2012/0143049 A1* | 6/2012 | Neubauer | A61B 90/98 |
| | | | 600/424 |
| 2013/0012807 A1* | 1/2013 | Al-Sunni | A61B 8/4254 |
| | | | 600/424 |
| 2014/0267773 A1 | 9/2014 | Jeung | |
| 2015/0170366 A1* | 6/2015 | Kruger | G01C 11/06 |
| | | | 382/103 |
| 2015/0356747 A1* | 12/2015 | Dielacher | G01S 17/023 |
| | | | 348/142 |

FOREIGN PATENT DOCUMENTS

| | | |
|---|---|---|
| JP | 2008026731 A | 2/2008 |
| JP | 2012117866 A | 6/2012 |
| WO | 199747240 A1 | 12/1997 |
| WO | 0100101 A1 | 1/2001 |
| WO | 200147413 A1 | 7/2001 |
| WO | 2006049787 A2 | 5/2006 |
| WO | 200713815 A2 | 10/2007 |

OTHER PUBLICATIONS

Olivo, Jacopo et al "Electronic Implants: Power Delivery and Management", Swiss National Science Foundation, 2013.

Nichia Corporation Specifications for Warm White LED, NESL157AT-H3, 2012.

Avago Technologies, HSMW-Cxxx White ChipLEDs Data Sheet, 2006.

\* cited by examiner

PULSED-LIGHT EMITTING MARKER DEVICE

CROSS-REFERENCE TO PRIOR APPLICATIONS

This application is the U.S. National Phase application under 35 U.S.C. § 371 of International Application No. PCT/EP2015/079513, filed on Dec. 14, 2015, which claims the benefit of European Patent Application No. 14198296.7, filed on Dec. 16, 2014. These applications are hereby incorporated by reference herein.

FIELD OF THE INVENTION

The invention relates to marking and/or tracking a region of interest of a human body. In particular, the invention relates to an active marker device, a tracking system, and an examination apparatus.

BACKGROUND OF THE INVENTION

In surgery, there may be a need to provide intra-operative imaging. This is because the anatomy that has been imaged pre-operatively may change significantly during surgery. For example, deformations may be caused by tissue cutting or by the movement of an organ, e.g. the liver, in the human body. Thus, there may be a significant non-linear deformation of the tissue and a simple registration of intra-operative imaging with pre-operative imaging may be difficult.

For this purpose, it is known to use tissue markers in order to find back the relevant tissue identified in pre-operative imaging during a subsequent procedure. Such markers are introduced into the tissue during the pre-operative phase. For example, X-ray absorbing markers may be used that are visible in an X-ray image acquired intra-operatively.

However, the usage of X-rays during surgery should be limited, not only to limit a dose of harmful radiation received by a patient, but also for example due to the fact that the surgery environment has to be sterile. This is more difficult when applying X-ray imaging, as intraoperative X-ray imaging requires the surgeon to wear for example lead shielding cloths, which may be inconvenient.

SUMMARY OF THE INVENTION

There may be a need to provide a marking device adapted for a precise and reliable marking of an object of interest of a human body.

A first aspect of the invention relates to a marker device being introducable into a tissue for marking a region of interest of a subject, such as a body of a patient. The marker device comprises a light source adapted for emitting light such that the marker device is visible to an optical sensor. Furthermore, the marker device comprises a switch adapted for operating the light source in a pulsed mode.

Hereinafter, a marker device according to the invention is also referred to as an "active marker device", i.e. a marker device comprising an active emitter, in particular a light source. This is contrary to "passive" marker devices, such as an X-ray absorbing marker.

A gist of the invention may be seen in providing an optical marker for tracking and/or registering an object or region of interest of a human body. For this purpose, the active marker device described in the context of the invention is provided.

It may be understood that the light source of the active marker device is in particular configured for emitting pulsed light.

The active marker can be implanted into the body during a pre-operative phase. During a subsequent procedure, the active marker device can be tracked using a suitable tracking device, which preferably comprises an optical sensor and more preferably at least one time-of-flight camera. Thus, the marked tissue structures can directly be linked to the coordinate system in the surgery room, and for example also to the coordinate system of a medical imaging system, such as an X-ray system.

By emitting pulsed light, the active marker device consumes less electrical power. Moreover, the active marker device emitting pulsed light can be detected more reliably by a time-of-flight camera. Further, the pulsed light emitted from the active marker device is better distinguishable from surrounding light, e.g. light emitted by a surgical task light or by lighting fixtures in the ceiling of the operating room, than a static light source.

In addition, the active marker device may be identifiable through a property of the pulsed light, e.g., the frequency or a specific pulse pattern. A further advantage of pulsing a LED may be the ability to over-drive the LED, i.e. the peak power may be larger than the maximum average power. In this way, the average LED temperature may be lower such that efficiency is improved and brighter light flashes may be emitted from the LED.

Although the active marker device is described for being introducible into a human tissue, the active marker device may be adapted for being introduced into animal tissue, e.g., for veterinary purposes. Moreover, the active marker device may be adapted for being introduced into dead tissue, e.g., for pathology.

The active marker device thus relates to a temporarily implantable light emitting marker, which is adapted for being detected outside the body, for example during a medical procedure. Preferably, the active marker device is adapted for emitting light pulses that can be detected with a time-of-flight camera. The active marker device may comprise an epoxy resin (e.g. EPO-TEK 301) into which the electronic components of the active marker device (e.g. the light source and the switch) are encapsulated. In other words, the active marker device may comprise a capsule into which the light source and the switch and other components may be encapsulated. The capsule of the active marker device may comprise an elongated shape and may fit into a cannula of an insertion needle.

The light source may be a light emitting diode (LED), e.g., a low power LED or a semiconductor laser diode. The light source may also be another kind of light source having a low power consumption and a small size.

The light source may be configured to emit light with a luminous intensity greater than 150 mcd, preferably greater than 500 mcd, even more preferred, greater than 1000 mcd. Furthermore, the light source may be configured to emit light with a luminous flux greater than 1 lm, preferably greater than 5 lm, even more preferred greater than 10 lm.

The switch may relate to an electronic circuit for switching on and off the light source and for operating the light source in the pulsed mode. There may be different possibilities how the switch can be structured. For example, the switch may be a mechanical switch such that the active marker device may be manually activated by operating the switch, e.g., just prior to the implantation of the active marker device. The switch may for example be operated by pressing a miniature button.

Furthermore, the switch may be adapted for being operated in a contactless manner such that the light source of the active marker device can be remotely activated, i.e. activated from outside a patient's body, in a contactless manner, for example after the active marker device has been temporarily implanted into body tissue. For example, the light source may be activated by means of a magnetic field. For being activated with a magnetic field, the switch may for example comprise a miniature bi-stable reed switch. Furthermore, the switch may comprise an electronic fuse which may be activated via RF pulses. The switch may also comprise phase change materials. The phase change of the phase change material can for example be induced by an external heating or by the body heat when the active marker is introduced into the body. In this case, the switch may be operated by an expansion or contraction of the phase change material which causes a mechanical force (e.g. a pressure) onto a mechanical switch such that an electrical circuit is closed. The switch may alternatively comprise a material which changes its electrical conductivity upon a phase change of the material for operating the switch.

The switch may comprise an electrical circuit for operating the light source in the pulsed mode. For example, the switch may comprise a timer for operating the light source in the pulsed mode. Furthermore, the switch may comprise a receiving unit for being triggered remotely. In other words, the light source may be operated to emit separated pulses of light. The pulsed mode of the light source may for example be characterized by a frequency of the pulses. The frequency may for example be between 0.1 Hz and 100 MHz. In other words, a pulsed mode may relate to a frequency with which the pulsed light is emitted by the light source. The pulse duration may be, e.g., 50% of the duty cycle of the pulsed mode of the light source. However, the pulse duration may also be more or less than 50% of the duty cycle. Alternatively or additionally, the pulsed mode may be characterized by one or more specific pulse patterns.

Furthermore, it is possible to provide a plurality of active marker devices, wherein each marker device emits light with a different pulsed mode, e.g. with a different frequency of pulses or a different pulse pattern. Moreover, each active marker device of the plurality of active marker devices may be uniquely identifiable via the pulsed mode.

According to an exemplary embodiment of the invention the switch is configured for operating the light source in a plurality of different pulsed modes. Furthermore, the switch is configurable for operating the light source in one specific pulsed mode of the plurality of different pulsed modes.

In this way, a plurality of active marker devices can be used for tracking an object of interest, wherein each active marker device has its own pulsed mode and is uniquely identifiable via its pulsed mode.

For example, the switch can be adapted for operating the light source with different frequencies. The switch may be programmable to emit light with a specific pulsed mode, e.g. a specific frequency, or a specific pulse pattern. The switch may also comprise a mechanic switch for mechanically switching between different pulsed modes. Furthermore, the switch may comprise a receiving unit for receiving an information about the pulsed mode with which the light source shall emit light.

According to a further exemplary embodiment of the invention, the active marker device further comprises a receiving unit adapted for receiving an activation signal for the light source. Moreover, the switch is configured to switch the light source on when the receiving unit receives the activation signal. The receiving unit may be encapsulated in a capsule of the active marker device.

The receiving unit may be a wireless receiving unit, e.g. an RF (radio frequency) antenna. The switch may be adapted for operating the light source in the pulsed mode, only when the receiving unit receives the activation signal, e.g. only when the RF antenna receives a radio signal.

In this way, the active marker device can be activated remotely, when the object of interest is to be tracked optically. Thus, it may be ensured that the active marker device only consumes electrical power while it is being used for tracking the object of interest.

According to a further exemplary embodiment of the invention, the receiving unit is configured for receiving a signal comprising information about a property of the pulsed mode. Furthermore, the switch is configured for operating the light source in the pulsed mode having said property.

The property of the pulsed mode may for example be a frequency of the pulses emitted by the light source.

In this way, a signal can be sent to the active marker device such that the active marker device emits light in a specific pulsed mode. Thus, the active marker device can be operated to emit light in a specific pulsed mode such that the light can be processed by an optical sensor and a processing unit coupled to said optical sensor, e.g., for identifying the marker device.

According to a further exemplary embodiment of the invention, the receiving unit is configured for receiving a triggering signal triggering the generation of a pulse by the light source. Furthermore, the switch is configured for turning the light source on, only when the triggering signal is received by the receiving unit.

In other words, the pulses generated by the light source can be triggered by an external triggering signal, e.g. a RF triggering signal. In this way, the pulsed mode can be defined by an external source emitting the signal triggering the pulses of the light source. Thus, the specific pulsed mode can be determined during the operation of the active marker device and does not need to be determined before implanting the active marker device.

According to a further exemplary embodiment of the invention, the active marker device further comprises an energy source adapted for supplying the light source with electrical energy.

The energy source may be encapsulated in a capsule of the active marker device.

According to a further exemplary embodiment of the invention, the energy source comprises a battery.

To provide power for the light source, the energy source may comprise a Lithium-ion battery. Moreover, the battery can be configured to provide energy to the light source only for less than 24 hours, preferably less than 10 hours, even more preferable less than 5 hours, since the active marker only needs to emit light during surgery. Thus, the battery can be made small enough such that it is prevented that the active marker device becomes bulky.

According to a further exemplary embodiment of the invention, the energy source comprises an LC circuit for a wireless power supply of the energy source.

According to a further exemplary embodiment of the invention, the active marker device is configured for being introduced into a cannula of an insertion needle.

For example, the active marker device can have an outer diameter which is smaller than 2.4 mm. Moreover, the active marker device may have dimensions such that it fits into the channel of 16 gauge, preferably 14 gauge, even more preferred 11 gauge, of an insertion needle.

According to a further exemplary embodiment of the invention, the light source is configured for emitting light with a wavelength in the range between 600 nm and 1300 nm, preferably between 700 nm and 1000 nm.

For said range of wavelength the human tissue may have a low absorption which allows the active marker device to be tracked even deep inside the tissue.

The light source may alternatively be configured to emit light with a wavelength, which is absorbed by the tissue to a greater extent. In this way, not only the active marker can be found but it can also enhance the visibility of the tissue structure to the physician.

Furthermore, the active marker device can also be configured to be used in conjunction with a contrast agent that has been injected into the patient. Since the light source may be inserted into the tissue, a good illumination of the contrast agent (which may be a fluorescent contrast agent) can be achieved.

A second aspect of the invention relates to a tracking system for tracking an object of interest of a human tissue. The tracking system comprises an active marker described in the context of the invention and an optical sensor adapted for detecting the light emitted by the light source of the active marker device. Furthermore, the tracking system comprises a processing unit adapted for determining a position of the active marker device on the basis of the light detected by the optical sensor.

In other words, the tracking system can be configured for determining a position of the active marker device on an optical basis. The optical sensor of the tracking system may have imaging capabilities. For example, the optical sensor may be an optical camera. The optical sensor may also be configured to detect infrared light emitted by the light source of the active marker device.

According to a further exemplary embodiment, the optical sensor comprises at least two optical cameras. Furthermore, the processing unit is configured for performing a triangulation on the basis of images recorded by the at least two optical cameras for determining the position of the active marker device.

According to an exemplary embodiment of the invention, the optical sensor comprises at least one time-of-flight camera for receiving the light emitted by the active marker device. The processing unit is configured for determining the position of the active marker device by triangulation.

As is understood in the art, a time-of-flight (TOF) camera is a camera that produces a depth image; each pixel of such camera encodes the distance to a corresponding point in the field of view of the camera. TOF cameras are typically configured to measure phase delays of incoming light, in accordance to the invention in particular light pulses emitted by an active marker device.

According to an exemplary embodiment, the processing unit is configured for determining three spherical surfaces, on which the active marker device is located. Furthermore, the processing unit is configured for determining the position of the marker device by determining an intersection of the three spherical surfaces. In other words, the position of the active marker device in 3D space can be determined. Information associated with the receipt of a light pulse emitted by the active marker device by at least one pixel of a TOF camera, such as the estimated time of flight of the light pulse, can be used for determining the path length between the active marker device and a surface point, for example a point on an exterior surface of a patient associated with the at least one pixel of the TOF camera. Thus, a spherical surface can be determined in 3D space on which the active marker device is located. By determining the intersection point of three such spherical surfaces, the marker location in 3D space can be identified with high accuracy.

For example, the optical sensor comprises a single time-of-flight camera, which comprises at least three image points or pixels. The time-of-flight camera may comprise at least three pixels for receiving the light emitted by the marker device, wherein the processing unit may be configured for determining a spherical surface for each one of the at least three pixels. Furthermore, the processing unit may be configured for determining the position of the marker device by determining an intersection of the three spherical surfaces.

The tracking system can be configured to determine the position of the active marker device in that different pixels of a single time-of-flight camera receive a light pulse of the active marker device emitted from a plurality of corresponding points (e.g. 3 points) on the surface of the body. Moreover, the tracking system can be configured to determine the position of said points on the surface of the body, e.g. during the registration procedure and/or by a standard reflective time-of-flight measurement. As the positions of the points on the surface of the body are known, the tracking system may be configured to determine the distance between each of said points on the surface and the active marker device from a phase delay in signals of the TOF camera signals representing a receipt of the emitted light pulse at the different pixels. Thus, the tracking system can be configured for triangulating the position of the active marker device, i.e. determining spherical surfaces for each of said points and for determining the intersection of the spherical surfaces yielding the position of the active marker device.

The tracking system may be configured for triggering a pulse of the light source of the active marker device, e.g. by emitting a RF signal. Furthermore, the tracking system may be configured for determining the time period between transmitting the RF signal for triggering the pulse of the light source and between detecting the pulse by the time-of-flight camera. In this way, the tracking device can determine the distance between the active marker device and each time-of-flight camera.

Moreover, the tracking system may also comprise more than one time-of-flight camera for improving the robustness of the system. In this way, the position in 3D space can also be determined if one camera cannot capture the light of the active marker device. Furthermore, the tracking system may be configured for taking into account light propagation time between tissue and air in order to determine the distance between the active marker device and the time-of-flight camera more accurately. For example, the distance between the each time-of-flight camera and the active marker device can be estimated using a patient surface model which may be registered in the surgical setup.

According to a further exemplary embodiment of the invention, the processing unit is configured for identifying the active marker device on the basis of the pulsed mode of the light received by the camera.

For example, the processing unit can identify the active marker device on the basis of the frequency of the pulses emitted by the light source.

According to a further exemplary embodiment of the invention, the tracking system further comprises a transmitting unit for transmitting an activation signal to the marker device.

A third aspect of the invention relates to a medical examination apparatus, comprising a medical imaging apparatus and a tracking system described in the context of the invention.

The medical imaging apparatus may be an X-ray device, a MRI, a US, a PET-CT or another imaging device. For example, the medical imaging apparatus may comprise a C-arm, on which the optical sensor or sensors of the tracking system is or are attached.

Furthermore, the exact position of the active marker device may be determined first by the imaging device, e.g. the X-ray system or other modality (MRI, X-ray, CT, US). Once the exact position of the active marker device is known, small movements of the active marker device can be tracked with the cameras with high precision.

These and other aspects of the invention will be apparent from and elucidated with reference to the embodiments described hereinafter.

BRIEF DESCRIPTION OF THE DRAWINGS

The figures are schematic and not true to scale. If in the following description elements of different figures are labeled with the same reference signs, they refer to the same or similar elements. The same or similar elements may, however, also be labeled with different reference signs.

DETAILED DESCRIPTION OF EMBODIMENTS

Figure 1:
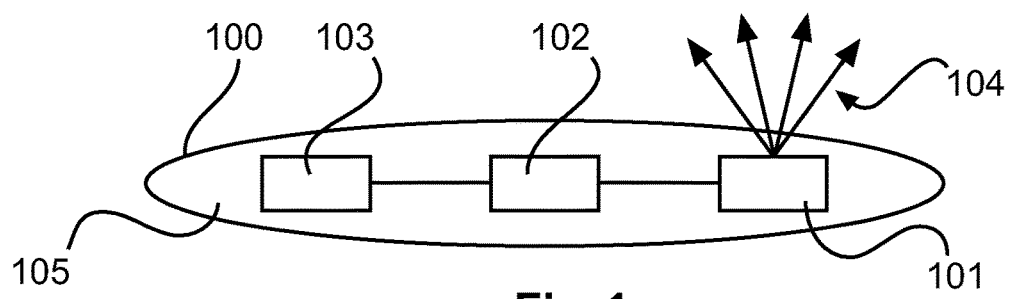
FIG. 1 shows an active marker device according to an exemplary embodiment of the invention.

In FIG. 1, an active marker device 100 according to an exemplary embodiment of the invention is shown. The active marker device is adapted for being introduced into human tissue for marking and for tracking an object of interest, e.g. a tumor, of a human body. The active marker device comprises 100 a light source 101 adapted for emitting light 104 such that the active marker device 100 is visible to an optical sensor. In an embodiment, the light source 101 may be a low power LED, for example. Furthermore, the active marker device 100 comprises a switch 102 adapted for turning the light source 101 on and off and for operating the light source 101 in a pulsed mode. Furthermore, the active marker device 100 comprises an energy source 103, e.g. a battery or a LC circuit for wireless power transfer to the active marker device 100. The light source 101, the switch 102, and the energy source 103 are encapsulated in a capsule 105 of the active marker device 100.

For example, the active marker device 100 comprises a low power LED 101 such as a Nichia NESL 157AT-H3 LED. This LED typically has a luminous flux of 11.5 lm and a luminous intensity of 4.0 cd. The LED 101 may, e.g., be connected to a small battery 103 and the switch 102 may be switchable from the distance. The LED can also be an HSMW white ChipLED having a size of 1.5×0.8×0.6 mm. Furthermore, the LED can be a PICOLED of ROHM having a size of 1.0×0.52×0.2 mm. The LED and the electronics of the active marker 100 may be capsulated in a capsule 105 of epoxy resin (e.g. EPO-TEK 301) that is biocompatible and optically transparent. The capsule 105 is made in an elongated shape such that it fits inside a cannula of an insertion needle.

Figure 2A:
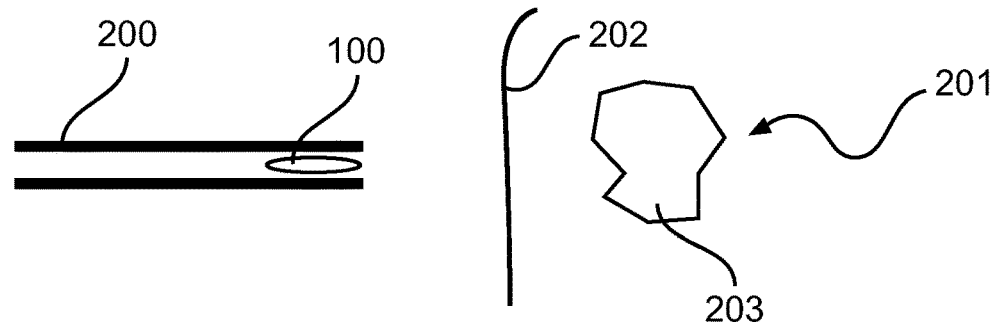
FIGS. 2A, 2B and 2C show the introduction of an active marker device according to an exemplary embodiment into a human tissue.
Figure 2B:
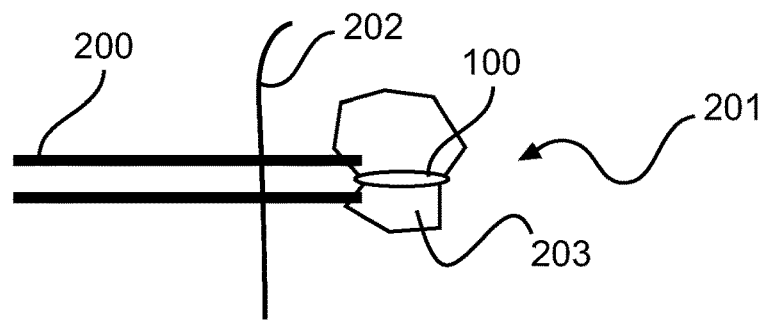
Figure 2C:
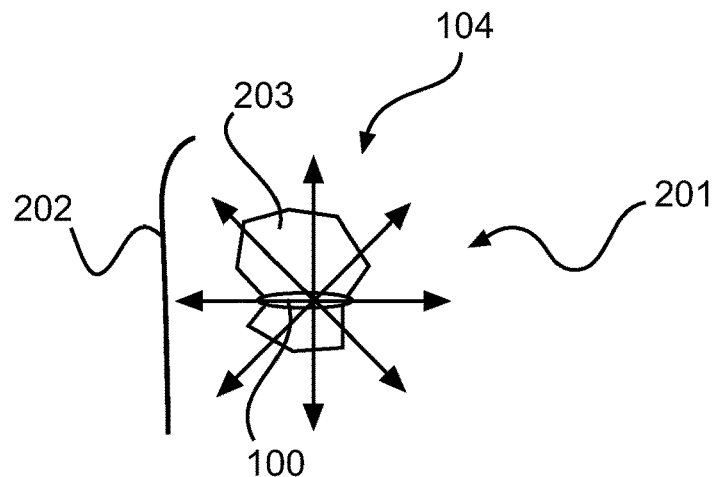

In FIGS. 2A to 2C the introduction of an active marker device 100 according to an exemplary embodiment of the invention into a body 201 (e.g., a human body) is shown. The active marker device 100 is located in a cannula of an insertion needle 200. The body 201 comprises a region of interest 203, e.g. a tumor. Furthermore, the human body has a body surface 202.

In FIG. 2B, the introduction or insertion of the active marker device 100 into the body 201 at or near the region of interest 203 is shown. For that purpose, the insertion needle 200 is pierced into the body 201 through the body surface 202 and the active marker device 100 is implanted in or near the region of interest 203.

In FIG. 2C, it is shown that the active marker device 100 implanted in or near the region of interest 203 emits light 104 in a pulsed mode for tracking the active marker device 100 and the region of interest 203, respectively. The light source of the active marker device 100 can be activated before implanting the active marker device into the body 201, e.g. by manually operating a switch. Alternatively, the light source can be activated in a contactless manner when the active marker device is already implanted in the body 201, e.g. by sending an RF activation signal.

Figure 3A:
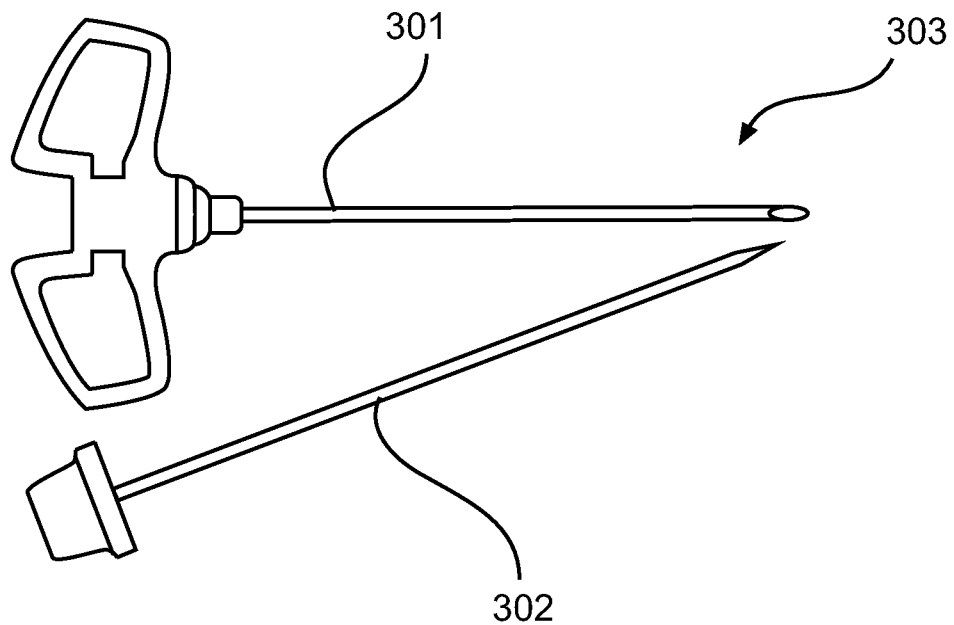
FIGS. 3A and 3B show insertion needle comprising a cannula, into which an active marker device according to an exemplary embodiment is introduced.
Figure 3B:
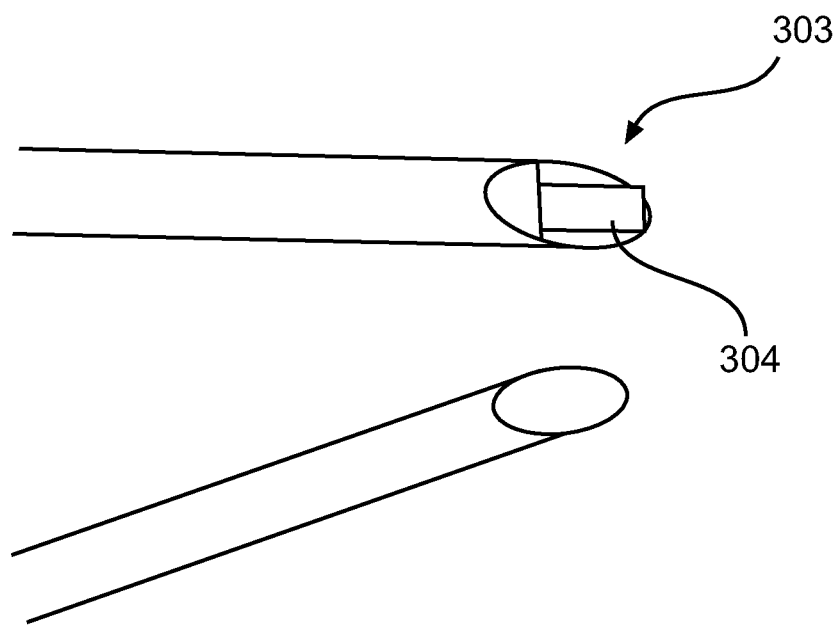

FIG. 3A shows an insertion needle 301 and a stylet 302, the insertion needle 301 comprising a cannula 303 for introducing an active marker device according to an exemplary embodiment of the invention. In FIG. 3B, an enlarged section of the cannula 303 is shown. It can be gathered that an active marker device is located inside the cannula 303 of the insertion needle.

Figures 4A, 4B:
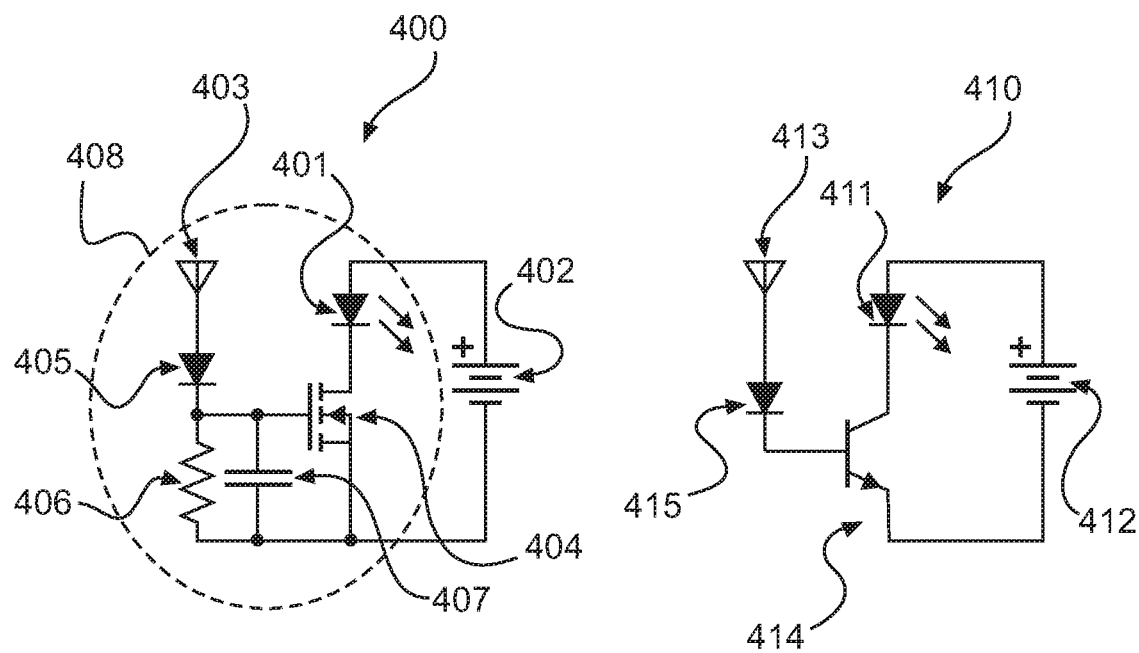
FIGS. 4A and 4B show electrical circuits for an active marker device according to exemplary embodiments of the invention.

FIG. 4A shows an example electrical circuit 400 for operating the light source 401 of the active marker device according to an exemplary embodiment of the invention. The light source is embodied as a light emitting diode (LED) 401. Furthermore, the electrical circuit comprises an energy source 402, e.g. a battery. Moreover, the light source 401 is coupled to a switching circuit 408 comprising a field-effective transistor 404, an RF antenna 403, a diode 405, a resistor 406, and a capacitor 407. The RF antenna 403, the diode 405, the resistor 406, and the capacitor 407 are part of an AM receiver of the switching circuit 408. FIG. 4B shows a simple circuit 410 for operating the light source 411 of the active marker device according to an exemplary embodiment of the invention. Again, the light source 411 is embodied as a light emitting diode (LED). In this case, the AM receiver comprises the RF antenna 413, the diode 415, and the transistor 414 and uses the input capacitance of the transistor 414.

Figure 5:
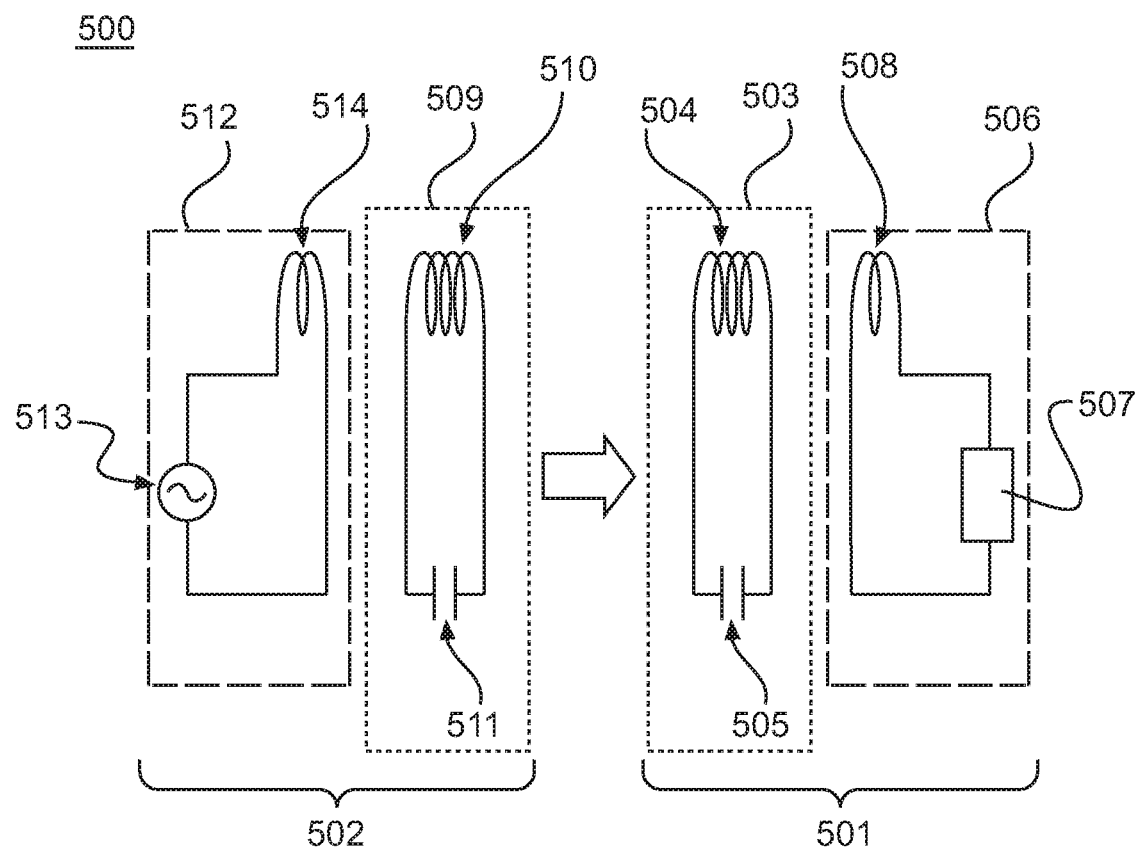
FIG. 5 shows an electrical circuit for wirelessly providing an active marker device with electrical energy.

In FIG. 5, an electrical circuit 501 and an energy supplying device 502 for wirelessly providing an active marker device 500 with electrical energy are shown.

The electrical circuit 501 comprises an LC circuit 503 having a coil 504 and a capacitor 505. Furthermore, the electrical circuit 501 comprises a load circuit 506 including a coil 508 and a LED driving electronics 507.

The electrical energy is wirelessly provided to the electrical circuit 501 by the energy supplying device 502. The energy supplying device 502 comprises an LC circuit 509 including a coil 510 and a capacitor 511. The energy supplying device 502 further comprises a source circuit including an alternating energy source and a coil 514.

The source circuit 512 is configured to couple the energy into the resonant LC circuit 509 via the coils 514 and 510. The LC circuit 503 of the active marker device receives a part of the electromagnetic flux generated by the LC circuit 509 and couples the energy into the load circuit 506 which supplies the LED driver electronics with electrical energy.

Figure 6:
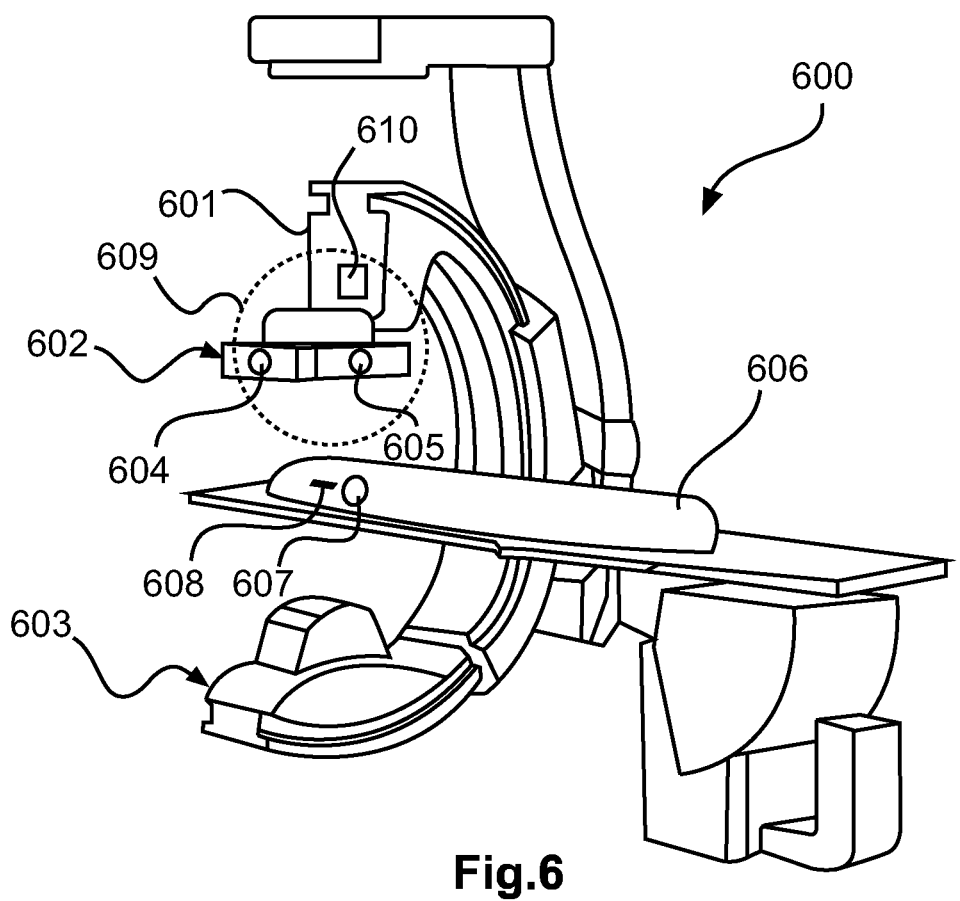
FIG. 6 shows a medical examination apparatus according to an exemplary embodiment.

In FIG. 6, a medical examination system 600 comprising a medical imaging apparatus 601 according to an exemplary embodiment of the invention is shown. In this exemplary embodiment, the medical imaging apparatus 601 comprises a C-arm having an X-ray source 603 and an X-ray detector 602. The medical imaging apparatus 601 (e.g., a C-arm) further comprises a tracking system having optical sensors 604 and 605 as well as a processing unit 610.

Furthermore, a human body 606 is located between the X-ray source 603 and the X-ray detector 602 of the C-arm. The human body 606 comprises a region of interest, e.g. a tumor. Moreover, an active marker device 608 is implanted into the human body at or near the region of interest 607. In this way, the active marker device 608 and/or the region of interest can be tracked without having to activate the X-ray source, e.g., when the human body is moved during surgery. The processing unit 610 is adapted for determining a position, e.g. a 3D position, of the active marker device 608 on the basis of the light detected by the optical sensors 604, 605. The processing unit 610 is adapted to determine the position of the active marker device 608 by applying triangulation.

Figure 7:
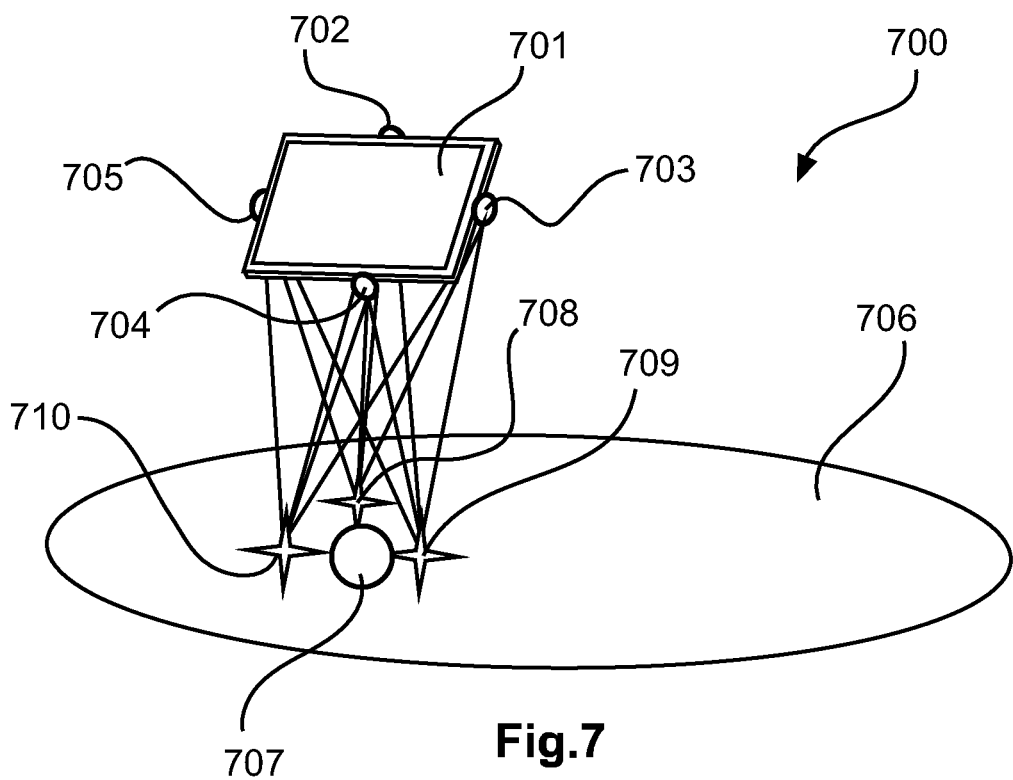
FIG. 7 shows a tracking system according to an exemplary embodiment of the invention.

In FIG. 7 a tracking system 700 according to an exemplary embodiment of the invention is shown. The tracking system comprises a support structure 701 for the time-of-flight cameras 702, 703, 704, 705. The support structure 701 is, e.g., a C-arm of a medical examination apparatus.

A body of a patient 706 having a tumor (region of interest) 707 is schematically shown. Furthermore, three implanted active marker devices 708, 709 and 710 circumscribing the tumor are shown. The tracking system 700 is configured for determining the position of the implanted active marker devices 708, 709 and 710 by determining an intersection of the three spherical surfaces determined by at least three time-of-flight cameras of the four time-of-flight cameras 702, 703, 704 and 705. In other words, the position of the active marker device in 3D space is determined using path information of the pulsed light emitted by the implanted active marker devices 708, 709, 710, as detected by the time-of-flight cameras. The estimated time of flight of the light pulse, which represents a path length for the emitted light from the active marker device to the camera, is used for determining the spherical surface on which the active marker device is located.

Figure 8A:
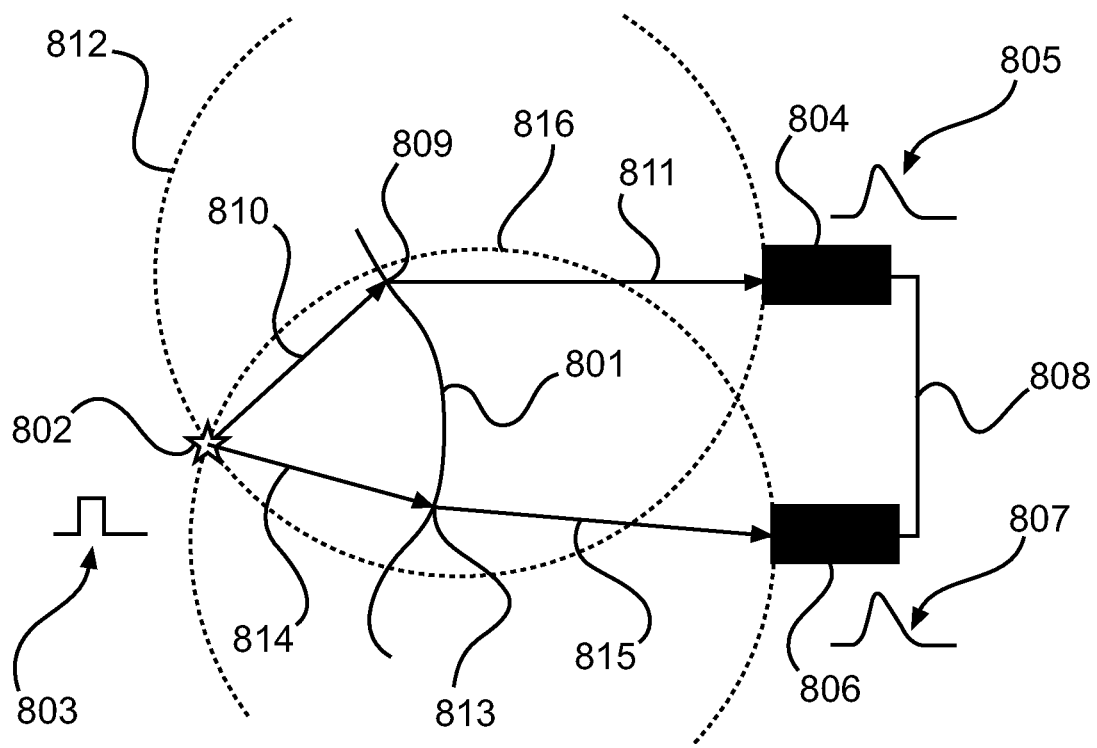
FIG. 8A shows a tracking system according to an exemplary embodiment of the invention.
Figure 8B:
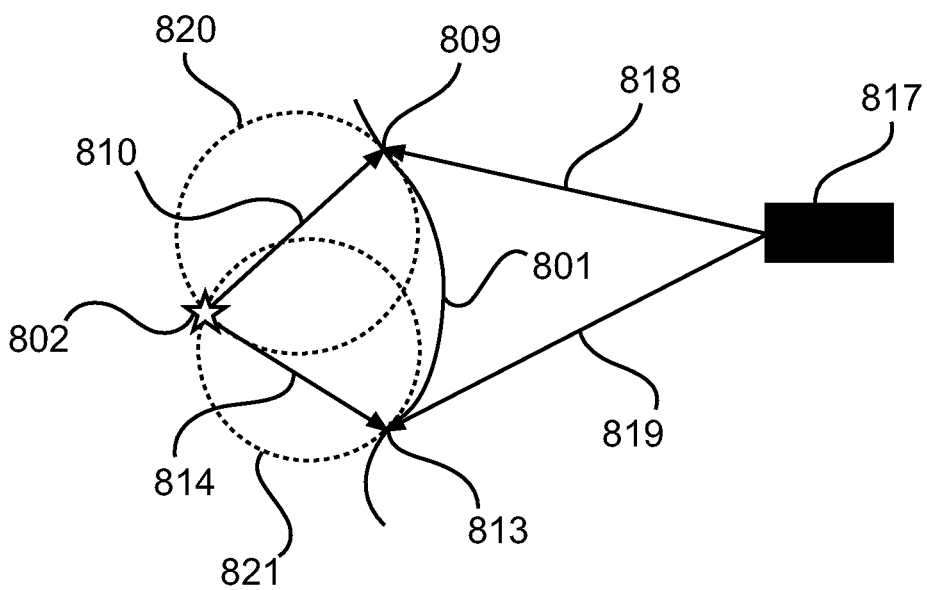
FIG. 8B shows a tracking system according to an exemplary embodiment of the invention.

In order to explain the working principle of the time-of-flight camera, exemplary embodiments in a simplified 2D representation are shown in FIGS. 8A and 8B.

In FIG. 8A a tracking system according to an embodiment of the invention is shown. Furthermore, a body having a surface 801 is depicted, in which an active marker device 802 is implanted. The active marker device 802 is configured to emit light in a pulsed mode. A signal curve 803 of the switch of the active marker device causing a light pulse of the active marker device 802 is further shown. The tracking system comprises a first time-of-flight camera 804 and a second time-of-flight camera 806. It is further shown that the first time-of-flight camera 804 generates a pulse-shaped signal 805 caused by the light pulse of the active marker device 802. The second time-of-flight camera 806 generates a pulse-shaped signal 807 caused by the light pulse of the active marker device 802. Furthermore, the tracking system comprises a device 808 for determining a phase delay between the pulse-shaped signals 805 and 807 of the first and second time-of-flight cameras 804 and 806. The phase delay between the pulse-shaped signals 805 and 807 correlates to the average path delay from the active marker device 802 to the surface 801 plus the distance from the surface 801 to the first and second time-of-flight cameras 804, 806. In other words, the phase delay corresponds to the difference in path length between the sum of the distances of the paths 810 and 811 and the sum of distances of the paths 814 and 815. The path 810 corresponds to the path between the active marker device 802 and the point 809 on the surface 801 and the path 811 corresponds to the path between the point 809 on the surface and the first time-of-flight camera 804. Equally, the path 814 corresponds to the path between the active marker device 802 and the point 813 on the surface 801 and the path 815 corresponds to the path between the point 813 on the surface and the second time-of-flight camera 806. In this way, the tracking system can triangulate the position of the active marker device 802 by determining the intersection of spherical surfaces 812 and 816.

Preferably, an additional third time-of-flight camera (not shown) may be used so that a 3D position of the active marker device 802 corresponds to a single intersection point of three spherical surfaces, one for each camera device.

In FIG. 8B, the determination of the position of the active marker device 802 with a single time-of-flight camera 817 is shown. A plurality of pixels of the time-of-flight camera receives the light pulse from the active marker. A first pixel receives the light being emitted from point 809 of the surface 801 of the body and a second pixel receives the light emitted from point 813 of the surface 801 of the body. For each of these of pixels, the distance between the camera and the corresponding points 809,813 on the patient surface is known, e.g. from registering the camera position with an existing patient outline scan, from standard reflective time-of-flight measurement or from any other suitable distance measurement.

At the first pixel that receives light from the point 809 on the surface 801, the measured value is composed of sum of the distances of paths 810 and 818. Equally, at the second pixel that receives light from the point 813 on the surface 801, the measured value is composed of sum of the distances of paths 814 and 819. Similar to the previous embodiment, the phase delay measured at the first and second pixel of the time-of-flight camera corresponds to the difference in path length between the sum of the paths 810 and 818 and the sum of the paths 814 and 819.

As the length of the paths 818 and 819 are known from the 3D position of points 809 and 813 and the 3D position of the single time-of-flight camera 817, the tracking system can determine the distances of paths 810 and 814 and subsequently triangulate the position of the active marker device by determining the intersection of spherical surfaces 820 and 821.

In 3D, preferably the position of the active marker device is determined using signals from at least three separate pixels of the time-of-flight camera. That is, based on a phase delay between these signals, the distances from the active marker device to at least three surface points observed by the corresponding pixels of the single time-of-flight camera may be determined. Again, the position of the active marker device is subsequently triangulated by determining the single intersection point of the three spherical surfaces corresponding to these distances.

A typical image may have many more surface points visible to different pixels of the TOF camera. Thus, preferably, signals from additional pixels receiving the light pulse from the marker at different time instances may be relied upon in order to further improve the accuracy of the marker position determination.

Optionally, a collimator may be used to restrict the image information received by the different pixels to a limited area of the total surface. That is, for example, the first pixel may receive light from the point 809 on the surface 801, but the collimator prevents light from surface point 813 from reaching the first pixel. Similarly, the collimator prevents light from the point 809 on the surface 801 from reaching the second pixel of the time-of-flight camera.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

LIST OF REFERENCE SIGNS

100 active marker device
101 light source
102 switch
103 energy source
104 light
105 capsule
200 insertion needle
201 human body
202 body surface
203 object of interest (e.g. tumor)
301 insertion needle
302 insertion needle
303 cannula
304 active marker device
400 electrical circuit
401 light source (LED)
402 energy source (battery)
403 receiving unit (RF antenna)
404 field effective transistor
405 diode
406 resistor
407 capacitor
410 electrical circuit
411 light source (LED)
412 energy source (battery)
413 receiving unit (RF antenna)
414 transistor
415 diode
500 active marker device
501 electrical circuit
502 energy supplying device
503 LC circuit
504 coil
505 capacitor
506 load circuit
507 LED driver electronics
508 coil
509 LC circuit
510 coil
511 capacitor
512 source circuit
513 alternating current source
514 coil
600 medical examination apparatus
601 C-arm
602 X-ray detector
603 X-ray source
604 optical sensor
605 optical sensor
606 body
607 region of interest (tumor)
608 active marker device
609 tracking system
610 processing unit
700 tracking system
701 camera support
702 time-of-flight camera
703 time-of-flight camera
704 time-of-flight camera
705 time-of-flight camera
706 body
707 region of interest (tumor)
708 active marker device
709 active marker device
710 active marker device
801 surface of the body
802 active marker device
803 signal of a light pulse
804 first time-of-flight camera
805 signal generated by the first time-of-flight camera
806 second time-of-flight camera
807 signal generated by the second time-of-flight camera
808 device for determining a phase delay
809 first point on the surface of the body
810 path between active marker and the first point
811 path between the first point and the first time-of-flight camera
812 first spherical surface
813 second point on the surface of the body
814 path between the active marker and the second point
815 path between the second point and the second time-of-flight camera
816 second spherical surface
817 single time-of-flight camera
818 distance between the first point and the single time-of-flight camera
819 distance between the second point and the single time-of-flight camera
820 first spherical surface
821 second spherical surface

The invention claimed is:

1. A tracking system for tracking a region of interest in a subject, comprising:
   an active marker device configured to be implanted into a tissue prior to a procedure for tracking a region of interest of a subject during the procedure, the active marker device comprising:
      a light source that emits light; and
      a switch configured to operate the light source in a pulsed mode, wherein the switch is configured to be operated in a contactless manner to remotely activate the light source during the procedure;
   an optical sensor disposed exterior to the subject and configured to detect light emitted by the light source of the active marker device implanted interior to the subject and emit pulse shaped signals, and to generate information associated with a receipt of light pulses, wherein the optical sensor comprises at least one time-of-flight camera; and
   a processor configured to determine a position of the active marker device based on the information from the optical sensor.

2. The tracking system according to claim 1, wherein the light source is configured for operation in a selectable one of a plurality of different pulsed modes and wherein the switch is configured to operate the light source in the selected one of the plurality of different pulsed modes.

3. The tracking system according to claim 2, further comprising: a receiver configured to receive an activation signal for the light source, wherein the switch is configured to switch the light source on in the selected one of the plurality of different pulsed modes when the receiver receives the activation signal.

4. The tracking system according to claim 3, wherein the receiver is configured to receive a triggering signal triggering the generation of pulses by the light source; and
   wherein the switch is configured to turn the light source on, only when the triggering signal is received by the receiver.

5. The tracking system of claim 2, wherein in each pulsed mode of the plurality of different pulsed modes, the light source operates at one or more frequencies.

6. The tracking system according to claim 2, wherein the switch further comprises a receiver configured to receive information regarding which of the plurality of different pulsed modes is to be selected.

7. The tracking system according to claim 2, wherein the processor is configured to identify the active marker device based on the selectable one of the plurality of different pulsed modes with which the light source is operated and the light pulses received by the optical sensor.

8. The tracking system according to claim 1, further comprising: a receiver configured to receive a signal comprising information about a property of the pulsed mode; and
   wherein the switch is configured to operate the light source in the pulsed mode having the property.

9. The tracking system according to claim 8,
   wherein the property of the pulsed mode is a frequency and/or a pulse pattern; and
   wherein the frequency and/or pulse pattern are selected to distinguish emitted light flashes from the light source from surrounding light including light emitted by surgical task lights and ceiling lighting fixtures.

10. The tracking system according to claim 1, further comprising:
    an energy source adapted to supply the light source with electrical energy.

11. The tracking system according to claim 10, wherein the energy source comprises an LC circuit configured for a wireless power supply of the energy source.

12. The tracking system according to claim 1, wherein the active marker device is configured to be introduced into a cannula of an insertion needle.

13. The tracking system according to claim 12, wherein the active marker device comprises a capsule into which the light source and the switch are encapsulated.

14. The tracking system according to claim 1, wherein the time-of-flight camera has at least three pixels configured to receive the light pulses emitted from the active marker device via a plurality of corresponding points on a surface of the subject, and wherein the processor is further configured to determine the position of the active marker device based on phase delays in signals of the time-of-flight camera representing the receipt of the light pulses at the at least three pixels.

15. A medical imaging and tracking system, comprising:
    the tracking system according to claim 1; and
    a medical imaging device.

16. The tracking system according to claim 1, wherein the light source has a pulse duration that is a percentage of a duty cycle of the pulsed mode of the light source.

17. The tracking system according to claim 1, wherein the light has a unique frequency or pulse pattern.

18. The tracking system according to claim 1, wherein the active marker device is uniquely identifiable by the its pulsed mode.

19. The tracking system according to claim 1, wherein the switch further comprises a timer.

20. The tracking system according to claim 1, wherein the optical sensor is a first optical sensor, and the tracking system further comprises a second optical sensor configured to generate additional information associated with the receipt of the light pulses.

21. The tracking system according to claim 20, wherein the time-of-flight camera is a first time-of-flight camera, and the second optical sensor comprises a second time-of-flight camera.

22. The tracking system according to claim 21, wherein the processor is further configured to determine the position of the active marker device based on the information from the first optical sensor and from the additional information from the second optical sensor.

23. A tracking system for tracking a region of interest in a subject comprising:
    an active marker device configured to be implanted into a tissue prior to a procedure for tracking a region of interest of a subject during the procedure, the active marker device comprising:
       a light source that emits light wherein the active marker device when implanted interior in the subject is detectable by an optical sensor disposed exterior to the subject; and
       a switch configured to operate the light source in a pulsed mode, wherein the switch is configured to be operated in a contactless manner for remotely activating the light source during the procedure;
    an optical sensor disposed exterior to the subject and configured to detect light pulses emitted by the light source of the active marker device implanted interior to the subject and emit pulse shaped signals, wherein the optical sensor comprises at least two time-of-flight cameras configured to receive the light pulses emitted by the active marker device and generating information associated with a receipt of the light pulses; and a processor configured to determine a position of the active marker device in the interior of the subject based on a phase delay between the pulse shaped signals emitted by the time-of-flight cameras in response to the light pulses emitted by the active marker device and received by the time-of-flight cameras.

* * * * *